(12) United States Patent
Koshio et al.

(10) Patent No.: US 8,569,211 B2
(45) Date of Patent: Oct. 29, 2013

(54) METHOD OF APPLYING A HERBICIDAL COMPOSITION

(75) Inventors: Kaihei Koshio, Tokyo (JP); Hirokazu Ohike, Hyogo (JP); Daijiro Shiino, Hyogo (JP); Masahiko Shimada, Hyogo (JP); Kuniaki Tsuruoka, Hyogo (JP); Aiko Yamanaka, Hyogo (JP)

(73) Assignee: NOF Corporation, Tokyo (JP)

( * ) Notice: Subject to any disclaimer, the term of this patent is extended or adjusted under 35 U.S.C. 154(b) by 410 days.

(21) Appl. No.: 12/918,224

(22) PCT Filed: Feb. 18, 2009

(86) PCT No.: PCT/JP2009/053305
§ 371 (c)(1),
(2), (4) Date: Nov. 3, 2010

(87) PCT Pub. No.: WO2009/104800
PCT Pub. Date: Aug. 27, 2009

(65) Prior Publication Data
US 2011/0045982 A1 Feb. 24, 2011

(30) Foreign Application Priority Data

Feb. 18, 2008 (JP) .................................. 2008-036634

(51) Int. Cl.
*A01N 37/00* (2006.01)
(52) U.S. Cl.
USPC .......................................... 504/307; 504/320
(58) Field of Classification Search
None
See application file for complete search history.

(56) References Cited

U.S. PATENT DOCUMENTS

| | | |
|---|---|---|
| 2,626,862 A | 1/1953 | Zimmerman et al. |
| 5,284,819 A | 2/1994 | Zorner et al. |

FOREIGN PATENT DOCUMENTS

| | | |
|---|---|---|
| JP | 39-17180 B1 | 8/1964 |
| JP | 48-000285 | 1/1973 |
| JP | 03-197402 A | 8/1991 |
| JP | 5-501254 A | 3/1993 |
| JP | 5-502216 A | 4/1993 |
| JP | 07-509692 A | 10/1995 |
| JP | 11-029411 A | 2/1999 |
| WO | WO 91/05471 A1 | 5/1991 |
| WO | WO 91/05472 A1 | 5/1991 |
| WO | WO 93/019598 A1 | 10/1993 |
| WO | WO9319598 * | 10/1993 |
| WO | WO 93/21768 A1 | 11/1993 |

OTHER PUBLICATIONS

Ohkawa et al, Plant growth inhibitory activity of fatty acids and the related compounds by the avena coleoptile test, Plant Science, 53, 1987, 35-38.*
Database WPI Accession No. XP-002991555 (1973-15780U), "Antifungal Treatment of Packaging Materials—using Monoglycerides of Caproic, Caprylic and Capric Acids" (Dec. 31, 1973).
Ohkawa et al., *Plant Science*, 53(1): 35-38 (1987).
Thormar et al., *Applied and Environmental Microbiology*, 72(1): 522-526 (2006).
Ghao Zhe, "Shanghai Food Science and Technology", Additive-Food Preservations, p. 56 (Apr. 30, 1984).
Chinese Patent Office, Search Report in Chinese Patent Application No. 200980105621.3 (Aug. 27, 2012).
European Patent Office, Extended European Search Report in European Patent Application No. 09713354.0-2103 (Sep. 26, 2012).

* cited by examiner

*Primary Examiner* — Alton Pryor
(74) *Attorney, Agent, or Firm* — Leydig, Voit & Mayer, Ltd.

(57) ABSTRACT

The invention provides a herbicidal composition containing, as an active ingredient, glycerol fatty acid ester obtained from fatty acid having an even-numbered carbon number of 6-12 and glycerol.

16 Claims, 3 Drawing Sheets

METHOD OF APPLYING A HERBICIDAL COMPOSITION

TECHNICAL FIELD

The present invention relates to a herbicidal composition with high safety on the environment.

BACKGROUND ART

Various weeds developed on agricultural land and nonagricultural land, and many herbicides have been developed and tried for eradication thereof. Not limited to agricultural land and nonagricultural land, since the habitat of human and the land where weeds are developed tend to be located near in recent years, herbicides not only superior in the effectiveness but also having higher safety for human and the environment have been demanded.

For example, both ragweed and giant ragweed are annual grasses of Compositae Ambrosia, and wind-pollinated flowers causing pollinosis. In North America where they are originated, many patients with ragweed pollinosis are developed in summer and autumn every year and, in Japan also, ragweed pollinosis patients are present next to cedar or Japanese cypress pollinosis patients. The pathogenesis of ragweed pollinosis is highly probably ragweed and giant ragweed that grow in the neighborhood, and therefore, eradication of ragweed and giant ragweed developed nearby is effective as a measure for preventing ragweed pollinosis.

Also from the aspect of environment beautification, eradication of ragweed and giant ragweed provides a high merit. Ragweed and giant ragweed have very high vitality, attach and grow around the world as naturalized plants, and destroy the ecosystem of the invaded area. From the aspects of environmentology and conservation ecology, therefore, eradication of ragweed and giant ragweed has been desired.

Heretofore, various chemical substances having herbicidal activity are known. Many chemical substances having herbicidal activity also show high toxicity to other organisms, and many of them are not easily decomposed. In contrast, biological fatty acid, a salt thereof and an ester thereof are known as herbicides comparatively safe to the environment.

Patent document 1 discloses suppression of plant growth and partial or whole killing by a dispersion of 0.3-10% undecylenoic acid or a derivative thereof. Patent document 2 discloses a herbicidal active concentrated liquid containing fatty acid having a carbon number of 8-12, oil and a surfactant, which is suitable for emulsification in water. Patent document 3 discloses a herbicidal emulsion composition containing fatty acid having a carbon number of 8-12, a surfactant and water. Patent document 4 discloses a plant growth control (herbicidal) composition containing diol such as ethylene glycol and the like and fatty acid ester having a carbon number of 6-20.

However, undecylenoic acid used in patent document 1 is expensive due to the starting material and the lengthy production step, since it is produced by purifying a thermally-decomposed material of castor oil. When fatty acid itself is used, moreover, the odor causes problems. Furthermore, pelargric acid frequently used in patent documents 2-4 is expensive, since it is produced by an oxidation reaction of oleic acid. Since fatty acid itself is used in patent documents 2 and 3, the odor sometimes causes problems. In patent document 4, since fatty acid ester is used, the odor can be suppressed low. However, since ethylene glycol monofatty acid ester has one hydroxyl group and is hydrophobic as a whole molecule, an emulsion is obtained when diluted with water, and a transparent uniform aqueous solution (solubilized liquid) superior in the long-term stability is difficult to obtain even in the co-presence of a surfactant and the like.

[patent document 1] U.S. Pat. No. 2,626,862
[patent document 2] JP-A-5-501254
[patent document 3] JP-A-5-502216
[patent document 4] JP-A-7-509692

DISCLOSURE OF THE INVENTION

Problems to be Solved by the Invention

The problem to be solved by the present invention is to provide a herbicidal composition that does not permit easy generation of fatty acid odor, shows low toxicity of decomposed material, is superior in the long-term stability, permits wide selectivity in obtaining the starting material, and is suitable for the environment.

Means of Solving the Problems

The present inventors have conducted intensive studies in an attempt to solve the aforementioned problems and found that fatty acid ester obtained from fatty acid having an even-numbered carbon number of 6-12 and glycerol can achieve the above-mentioned object, which resulted in the completion of the present invention.

Accordingly, the first invention is a herbicidal composition comprising, as an active ingredient, glycerol fatty acid ester obtained from fatty acid having an even-numbered carbon number of 6-12 and glycerol.

The second invention is the herbicidal composition described in the first invention, wherein the fatty acid having an even-numbered carbon number of 6-12 is caprylic acid.

The third invention is the herbicidal composition described in the first invention, wherein the fatty acid having an even-numbered carbon number of 6-12 is caproic acid.

The fourth invention is the herbicidal composition described in any one of the first to the third inventions, wherein the glycerol fatty acid ester is monoester.

The fifth invention is the herbicidal composition described in any one of the first to the fourth inventions, which is an emulsion or solubilized liquid containing 0.5-30 mass % of glycerol fatty acid ester.

The sixth invention is the herbicidal composition described in any one of the first to the fifth inventions, which is for ragweed or giant ragweed.

Effect of the Invention

According to the present invention, a herbicidal composition that does not permit easy generation of fatty acid odor, shows low toxicity of decomposed material, is superior in the long-term stability, permits wide selectivity in obtaining the starting material, and is suitable for the environment can be provided.

BEST MODE FOR CARRYING OUT THE INVENTION

Figure 1:
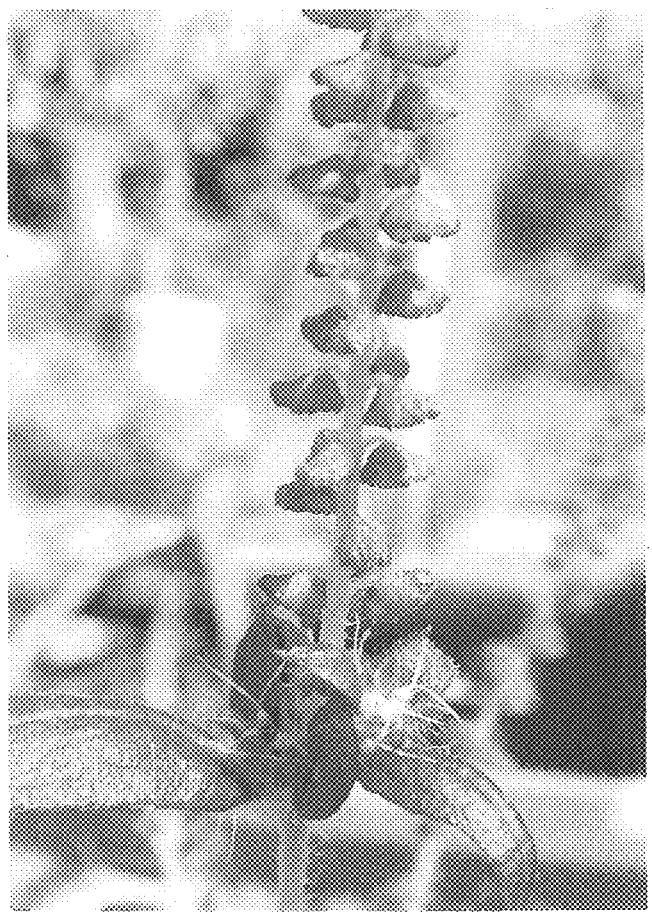
[FIG. 1] A photograph showing the state of ragweed in the control section.

The herbicidal composition of the present invention is explained in the following.

The herbicidal composition of the present invention is characterized in that it contains glycerol fatty acid ester obtained from fatty acid having an even-numbered carbon number of 6-12 and glycerol as an active ingredient.

The fatty acid constituting the glycerol fatty acid ester is preferably an even-numbered fatty acid from among those having a carbon number of 6-12 and strong herbicidal activity, which is specifically caproic acid, caprylic acid, capric acid or lauric acid. The number of addition of fatty acid constituting glycerol fatty acid ester can be any number from 1 to 3. Glycerol monocaproic acid ester and glycerol monocaprylic acid ester, wherein fatty acid is caproic acid or caprylic acid having a carbon number of 6 or 8 and fatty acid addition number is 1, are more preferable, since they have two hydroxyl groups and a small fatty acid moiety, and therefore, show relatively high hydrophilicity, and allow preparation of a transparent uniform aqueous solution (solubilized liquid) obviously superior in the long-term stability after dilution with water.

Glycerol fatty acid ester to be used in the present invention may be used alone. When used alone, however, its high viscosity increases the amount of use for application. For spraying, it requires heating to decrease viscosity and high-pressure spraying. Thus, it is effectively used as an or solubilized liquid.

The concentration of glycerol fatty acid ester in the emulsion or solubilized liquid is preferably 0.5-30 mass %, more preferably 1-20 mass %. When it is not more than 1 mass %, the application amount necessary for affording the effect increases, when it is less than 0.5 mass %, a sufficient effect is not easily afforded, when it is not less than 20 mass %, the emulsion has low stability which necessitates use immediately after preparation, and the solubilized liquid does not permit easy spraying due to its increased viscosity. When it is not less than 30 mass %, a stable emulsion is not easily afforded, and spraying of the solubilized liquid becomes difficult due to its increased viscosity.

The emulsion here means a solution in which a liquid insoluble in water is present in a particle state to optically scatter visible light, which looks white to the naked eye. On the other hand, a solubilized liquid means a solution in which the liquid is miscible with water at a level free of optical scattering of visible light, which looks transparent to the naked eye.

For production of an emulsion or solubilized liquid, a surfactant may be added to improve stability, and the surfactant to be added may be any as long as it is generally used as a surfactant, and a non-ionic surfactant is particularly preferable. Examples of the non-ionic surfactant include polyoxyethylene alkyl ether non-ionic surfactants, polyoxyethylene fatty acid ester non-ionic surfactants, polyoxyethylene fatty acid sorbitan ester non-ionic surfactants, polyoxyethylene hydrogenated castor oil non-ionic surfactants, polyoxyethylene glycerol fatty acid ester non-ionic surfactants, polyglycerol fatty acid ester non-ionic surfactants and the like.

Examples of the target plant for which the herbicidal composition of the present invention can be applied include Broad-leaved weeds such as Solanaceae weeds represented by black nightshade (*Solanum nigrum*), jimsonweed (*Datura stramonium*) and the like, Malvaceae weeds represented by velvetleaf (*Abutilon theophrasti*), prickly fanpetals (*Sida spinosa*) and the like, Convolvulaceae weeds represented by *Ipomoea* spps. such as tall morning-glory (*Ipomoea purpurea*) and the like and *Calystegia* spps., Amaranthaceae weeds represented by green amaranth (*Amaranthus lividus*) and the like, Compositae weed represented by cocklebur (*Xanthium strumarium*), ragweed (*Ambrosia artemisiaefolia*), giant ragweed (*Ambrosia trifida*), sunflower (*Helianthus annus*), hairy galinsoga (*Galinsoga ciliata*), Canada thistle (*Cirsium arvense*), groundsel (*Senecio vulgaris*), eastern daisy fleabane (*Erigeron annus*) and the like, Cruciferae weeds represented by variableleaf yellowcress (*Rorippa indica*), charlock (*Sinapis arvensis*), shepherd's-purse (*Capsellaurea bursa-pastoris*) and the like, Polygonaceae weeds represented by oriental lady's thumb (*Polygonum blumei*), black bindweed (*Polygonum convolvulus*) and the like, Portulacaceae weeds represented by purslane (*Portulaca oleracea*) and the like, Chenopodiaceae weeds represented by lambsquarters (*Chenopodium album*), figleaf goosefoot (*Chenopodium ficifolium*), kochia (*Kochia scoparia*) and the like, Caryophyllaceae weeds represented by chickweed (*Stellaria media*) and the like, Scrophulariaceae weeds represented by large field speedwell (*Veronica persica*) and the like, Commelinaceae seeds represented by dayflower (*Commelina communis*) and the like, Labia tae weeds represented by henbit (*Lamium amplexicaule*), purple dead-nettle (*Lamium purpureum*) and the like, Euphorbiaceae weeds represented by milk purslane (*Euphorbia supina*), spotted sandmat (*Euphorbia maculata*) and the like, Rubiaceae weeds represented by stickywilly (*Galium spurium*), catchweed (*Galium aparine*), madder (*Rubia akane*) and the like, Violaceae weeds represented by field pansy (*Viola arvensis*) and the like, Leguminosae weeds represented by bigpod sesbania (*Sesbania exaltata*), sickle senna (*Cassia obtusifolia*) and the like, and the like, Graminaceous weeds represented by wild sorghum (*Sorghum bicolor*), fall panicgrass (*Panicum dichotomiflorum*), Johnsongrass (*Sorghum halepense*), barnyardgrass (*Echinochloa crus-galli*), crabgrass (*Digitaria adscendens*), oat (*Avena fatua*), yard grass (*Eleusine indica*), bristle grass (*Setaria viridis*), meadow foxtail (*Alopecurus aequalis*) and the like, Cyperaceous weeds represented by nutgrass (*Cyperus rotundus, Cyperus esculentus*) and the like, Alismataceae weeds represented by heraomodaka (*Alisma canaliculatum*), threeleaf arrowhead (*Sagittaria trifolia*), dwarf arrowhead (*Sagittaria pygmaea*) and the like, Cyperaceae weeds represented by variable flatsedge (*Cyperus difformis*), tidalmarsh flatsedge (*Cyperus serotinus*), tule (*Scirpus juncoides*), kuroguwai (*Eleocharis kuroguwai*) and the like, Scrothuslariaceae weeds represented by false pimpernel (*Lindenia pyxidaria*) and the like, Potenderiaceae weeds represented by heartshape false pickerelweed (*Monochoria Vaginalis*) and the like, Potamogetonaceae weeds represented by Cape pondweed (*Potamogeton distinctus*) and the like, Lythraceae weeds represented by Indian toothcup (*Rotala indica*) and the like, Gramineae weeds represented by rice barnyardgrass (*Echinochloa crus-galli*) and the like, and the like.

The herbicidal composition of the present invention containing glycerol fatty acid ester as an active ingredient can also be used concurrently or in a mixture with other herbicides. Examples of the herbicides that can be used concurrently or in a mixture include phenoxy acid (acid, ester, salt) herbicides such as 2,4-D, MCPA, dichloroprop and the like, benzoic acid herbicides such as dicamba and the like, aryloxyphenoxypropionate (acid, ester, salt) herbicides such as fluazifop, diclofop and the like, sulfonylurea (acid, ester) herbicides such as chlorimuron, bensulfuron and the like, imidazolinone herbicides such as imazethapyr and the like, bipyridylium herbicides such as paraquat and the like, diphenylether (acid, salt) herbicides such as acifluorfen, fomesafen and the like, cyclohexanedione herbicides such as sethoxydim, cycloxydim, clethodim and the like, methane arsonate herbicides such as MSMA (arsonic acid, methyl) and the like, triazine herbicides such as atrazine, cyanazin and the like, aliphatic carboxylic acid herbicides such as dalapon and the like, benzonitrile herbicides such as bromoxynil and the like, carbamate herbicides such as Barban and the like, thiocarbamate herbicides such as benthiocarb, triallate and the like, pyrazon herbicides, glyphosate herbicides, picloram herbicides, metribuzin herbicides, gluphosinate herbicides, clopyralid herbicides, bentazon herbicides, desmedipham herbicides, quinclorac herbicides, amytal herbicides, phenmedipham herbicides, triclopyr herbicides, ethiozin herbicides, and the like.

EXAMPLES

The present invention is explained in more detail in the following by referring to Examples. In the Examples, "%" is based on mass.

Examples 1-7

Evaluation of Herbicidal Activity by Direct Application of Glycerol Fatty Acid Ester The base compound shown in Table 1 was directly applied to the ragweed transplanted and blooming in a planter filled with reddish soil of the loamy layer of the Kanto Plain, and the killing state of the floral leaves was visually confirmed after lapse of one day. The results are shown in Table 1.
(Evaluation of Odor by Direct Application of Glycerol Fatty Acid Ester)
The ragweed applied in the same manner was placed in a plastic bag (length 20 cm, width 14 cm) and the bag was tightly sealed. The odor was sensorily evaluated after lapse of one day. The results are shown in Table 1.
(Evaluation of Eye Irritancy of Hydrolysate)
Assuming that the base compound is hydrolyzed in the natural world, the biological reaction of hydrolysate was evaluated by eye irritancy. To be specific, the base compound (10 g) shown in Table 1 was added to 100 mL of water, and the mixture was adjusted to pH 10 with an aqueous sodium hydroxide solution. The mixture was placed in a flask, heated to 80° C., and stirred for 1 hr while adding an aqueous sodium hydroxide solution as appropriate every 10 min to maintain pH 10. The mixture was adjusted to pH 3.5 with an aqueous hydrochloric acid solution, and the mixture was washed 3 times with hexane to remove fatty acid. The solution was neutralized with an aqueous sodium hydroxide solution, evaporated and filtered to remove sodium chloride. The viscous liquid was diluted with purified water to a concentration of 50% and used as an eye irritancy measurement sample.

Using three male Japanese white rabbits per sample, the above-mentioned eye irritancy measurement sample (0.1 mL) was instilled into the unilateral intracapsular conjunctiva of each test animal, and the upper and lower eyelids were gently closed and maintained for about 1 sec. The other eye was used as control without treatment. After instillation, the cornea, iris, conjunctiva and the like were observed 1, 6, 12 and 24 hr later. The results are simultaneously shown in Table 1.

TABLE 1

| | base compound | herbicidal activity | odor | eye irritancy of hydrolysate |
|---|---|---|---|---|
| Ex. 1 | Glycerol tricaprylic acid ester | brown discoloration | slight odor | no problem *1 |
| Ex. 2 | Glycerol dicaprylic acid ester | markedly brown discoloration | slight odor | no problem *1 |
| Ex. 3 | Glycerol sesquicaprylic acid ester | markedly brown discoloration | slight odor | no problem *1 |
| Ex. 4 | Glycerol monocaprylic acid ester | brown discoloration | slight odor | no problem *1 |
| Ex. 5 | Glycerol monocaproic acid ester | markedly brown discoloration | slight odor | no problem *1 |
| Ex. 6 | Glycerol monocapric acid ester | markedly brown discoloration | slight odor | no problem *1 |
| Ex. 7 | Glycerol monolauric acid ester | brown discoloration | slight odor | no problem *1 |
| Comp. Ex. 1 | caproic acid | markedly brown discoloration | stink | — |
| Comp. Ex. 2 | pelargric acid | markedly brown discoloration | stink | — |
| Comp. Ex. 3 | undecylenoic acid | markedly brown discoloration | stink | — |
| Comp. Ex. 4 | ethylene glycol monopelargric acid ester | markedly brown discoloration | slight odor | problematic *2 |

In Table 1, *1 means that abnormality was not observed in the cornea, iris, conjunctiva and the like as compared to other non-treated eyes. *2 means that conjunctival hyperemia was observed in two rabbits.

Results

In Table 1, Examples 1-7 show the results of each of the above-mentioned evaluations using the herbicidal composition of the present invention. Comparative Examples 1-4 show the results of similar evaluations using caproic acid, pelargric acid, undecylenoic acid and ethylene glycol monopelargric acid ester.

From Table 1, the composition of the present invention used in Examples 1-7 discolored floral leaves of ragweed in brown or markedly discolored them in brown in the herbicidal activity evaluation. That is, by the evaluation of the herbicidal activity, the superior herbicidal activity of the herbicidal composition of the present invention was confirmed.

From Table 1, in the odor evaluation, the herbicidal composition of the present invention used in Examples 1-7 and the composition of Comparative Example 4 only slightly smelled but the compositions of Comparative Examples 1, 2 and 3 stank. This is attributable to the use of fatty acid itself in Comparative Examples 1, 2 and 3, whereas fatty acid ester was used in Examples 1-7 and Comparative Example 4. In other words, it was confirmed by the odor evaluation that the herbicidal composition of the present invention is a herbicidal composition that resists odor development.

From Table 1, the composition of the present invention used in Examples 1-7 in the evaluation of eye irritancy of the hydrolysate was free of problems, whereas the composition of Comparative Example 4 was problematic. That is, it was confirmed by the eye irritancy evaluation that the hydrolysate of the herbicidal composition of the present invention is free of toxicity.

From the herbicidal activity in Table 1, all the compositions of Examples 1-7 and Comparative Examples 1-4 showed an ideal herbicidal activity. Among them, the compositions of Examples 1-7 and Comparative Example 4 were evaluated to have resisted easy odor development in the odor evaluation and, moreover, the compositions of Examples 1-7 were confirmed to have produced no harmful stimulation to living organisms even after hydrolysis, from the test results of eye irritancy.

From the above, it has been confirmed that the herbicidal composition of the present invention affords a herbicidal composition which resists easy odor development, shows low toxicity of the decomposed material, has wide selectivity in the availability of the starting material, and is suitable for the environment.

Example 8

Evaluation by Spraying of Solubilized Liquid of Glycerol Fatty Acid Ester

Glycerol monoprylic acid ester (5 parts by mass), polyethylene glycol (20) monooleic acid sorbitan ester (1 part by mass) and water (94 parts by mass) were treated by a homogenizer (QUICK HOMO MIXER LR-1 manufactured by MIZUHO Industrial CO., LTD.) at 7000 rpm for 3 min to give a solubilized liquid containing 5 mass % of glycerol fatty acid ester. The solubilized liquid was applied to the ragweed and giant ragweed transplanted and blooming in a planter filled with reddish soil of the loamy layer of the Kanto Plain until the liquid dripped and the appearance was photographed one day later. Water was applied to the control section. The results are shown in the photograph of FIGS. 1-4.

Results

Figure 2:
[FIG. 2] A photograph showing the state of ragweed one day after spraying a solubilized liquid of glycerol fatty acid ester.
Figure 3:
[FIG. 3] A photograph showing the state of giant ragweed in the control section.
Figure 4:
[FIG. 4] A photograph showing the state of giant ragweed one day after spraying a solubilized liquid of glycerol fatty acid ester.

FIG. 1 and FIG. 3 show the state of ragweed and giant ragweed in the control section, and FIG. 2 and FIG. 4 show the state of ragweed and giant ragweed one day after application of the solubilized liquid of glycerol fatty acid ester.

As is clear from FIGS. 1-4, it was confirmed in the present invention that the herbicidal activity is high even in the form of a solubilized liquid.

Examples 9, 10

Stability Evaluation of Solubilized Liquid

Glycerol fatty acid ester was blended at the composition shown in Table 2, and the mixture was treated by a homogenizer (QUICK HOMO MIXER LR-1 manufactured by MIZUHO Industrial CO., LTD.) at 7000 rpm for 3 min to give a solubilized liquid containing 5 mass % of glycerol fatty acid ester. The solubilized liquid immediately after preparation was visually evaluated, and the solubilized liquid after standing in a cold dark place for 3 months was visually evaluated again. The results are shown in Table 2.

TABLE 2

| | blending composition | | | visual evaluation results | |
|---|---|---|---|---|---|
| | base compound | additive | dilution liquid | immediately after preparation | 3 months later |
| Ex. 9 | glycerol monocaprylic acid ester: 5 mass % | polyethylene glycol (20) monooleic acid sorbitan ester: 1 mass % | water: 94 mass % | transparent uniform aqueous solution | transparent uniform aqueous solution |
| Ex. 10 | glycerol monocaproic acid ester: 5 mass % | none | water: 95 mass % | transparent uniform aqueous solution | transparent uniform aqueous solution |

From Table 2, it has been confirmed that the compositions of Examples 9 and 10 are superior in the long-term stability, since they were transparent uniform aqueous solutions as if immediately after preparation, even after standing in a cold dark place for 3 months.

Generally, when emulsions of fatty acid and the like are stood for a long time, emulsion particles gather in the upper layer since the density of fatty acid is lower than that of water and, in some cases, emulsion particles assemble to form an oil layer. On the other hand, since the base compounds of Examples 9 and 10 are glycerol monocaproic acid ester and glycerol monocaprylic acid ester, which have two hydroxyl groups and a small fatty acid moiety, they have relatively high hydrophilicity, can provide transparent uniform aqueous solutions (solubilized liquids), and are free of surfacing and assembling of the emulsion particles due to difference in the specific gravity.

Example 11

Confirmation of Effect as Herbicides for Plant Species Other than Ragweed

The application liquids shown in Table 3 were applied to the plants shown in Table 3 at 50 mL/m$^2$ by a hand spray. To be specific, the liquids were sprayed 5 times using No. 505 manufactured by FURUPLA Co., LTD. from about 30 cm from the target. After lapse of one day, the states of the plant leaves and flowers were visually observed to evaluate the herbicidal activity. The results are shown in Table 3.

TABLE 3

| application liquids | plant species | herbicidal activity (state one day after application) |
|---|---|---|
| composition of Example 9 | eastern daisy fleabane | flowers and leaves were completely withered |
| water | eastern daisy fleabane | no change |
| composition of Example 9 | oriental lady's thumb | flowers and leaves were completely withered |
| water | oriental lady's thumb | no change |
| composition of Example 9 | dayflower | flowers and leaves were completely withered |

TABLE 3-continued

| application liquids | plant species | herbicidal activity (state one day after application) |
|---|---|---|
| water | dayflower | no change |
| composition of Example 9 | heartshape false pickerelweed | flowers and leaves were completely withered |
| water | heartshape false pickerelweed | no change |
| composition of Example 10 | eastern daisy fleabane | about 80% was withered |
| water | eastern daisy fleabane | no change |
| composition of Example 10 | oriental lady's thumb | about 70% was withered |
| water | oriental lady's thumb | no change |

From Table 3, it was confirmed that the herbicidal composition of the present invention shows herbicidal activity in all the examined plants. Since the medium chain fatty acid which is the starting material of glycerol fatty acid ester which is the base compound of the present invention has herbicidal activity for many plants, the herbicidal composition of the present invention can be considered to also have herbicidal activity for many plants.

INDUSTRIAL APPLICABILITY

According to the present invention, a herbicidal composition that does not permit easy generation of fatty acid odor, shows low toxicity of decomposed material, is superior in the long-term stability, permits wide selectivity in obtaining the starting material, and is suitable for the environment can be provided.

Since the herbicidal composition of the present invention has high herbicidal activity even in the form of an emulsion or solubilized liquid and hydrolysate thereof does not have toxicity, methods such as aerial application and the like are also effective, whereby weeds such as ragweed, giant ragweed and the like can be collectively eradicated over a wide area. That is, due to the above-mentioned advantages, the herbicidal composition of the present invention is effective for the prophylaxis of allergic diseases, particularly for adopting prophylactic measures for ragweed pollinosis, and further provides an effective solving means for the themes of environment beautification, conservation of biodiversity, and eradication of naturalized plants.

This application is based on patent application No. 2008-36634 (filing date: Feb. 18, 2008) filed in Japan, the contents of which are incorporated herein.

The invention claimed is:

1. A herbicidal method comprising applying, to a target plant selected from annual grasses and wind-pollinated flowers, an effective amount of a composition comprising, as an active ingredient, glycerol fatty acid ester obtained from fatty acid having a carbon number of 6 or 8 and glycerol.

2. The herbicidal method according to claim 1, wherein the fatty acid is caprylic acid.

3. The herbicidal method according to claim 1, wherein the fatty acid is caproic acid.

4. The herbicidal method according to claim 1, wherein the glycerol fatty acid ester is monoester.

5. The herbicidal method according to claim 1, wherein the composition is an emulsion or solubilized liquid containing 0.5-30 mass % of the glycerol fatty acid ester.

6. The herbicidal method according to claim 1, wherein the target plant is ragweed or giant ragweed.

7. The herbicidal method according to claim 2, the glycerol fatty acid ester is monoester.

8. The herbicidal method according to claim 3, the glycerol fatty acid ester is monoester.

9. The herbicidal method according to claim 2, wherein the composition is an emulsion or solubilized liquid containing 0.5-30 mass % of the glycerol fatty acid ester.

10. The herbicidal method according to claim 3, wherein the composition is an emulsion or solubilized liquid containing 0.5-30 mass % of the glycerol fatty acid ester.

11. The herbicidal method according to claim 4, wherein the composition is an emulsion or solubilized liquid containing 0.5-30 mass % of the glycerol fatty acid ester.

12. The herbicidal method according to claim 7, wherein the composition is an emulsion or solubilized liquid containing 0.5-30 mass % of the glycerol fatty acid ester.

13. The herbicidal method according to claim 8, wherein the composition is an emulsion or solubilized liquid containing 0.5-30 mass % of the glycerol fatty acid ester.

14. The herbicidal method according to claim 2, wherein the target plant is ragweed or giant ragweed.

15. The herbicidal method according to claim 7, wherein the target plant is ragweed or giant ragweed.

16. The herbicidal method according to claim 12, wherein the target plant is ragweed or giant ragweed.

* * * * *